US00PP30651P2

(12) United States Plant Patent
Hartman

(10) Patent No.: US PP30,651 P2
(45) Date of Patent: Jul. 2, 2019

(54) ***CALADIUM* PLANT NAMED 'BOTTLE ROCKET'**

(50) Latin Name: ***Caladium* X *hortulanum***
Varietal Denomination: Bottle Rocket

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 15/732,902

(22) Filed: Jan. 13, 2018

(51) Int. Cl.
*A01H 6/10* (2018.01)

(52) U.S. Cl.
USPC ..... Plt./373

(58) Field of Classification Search
USPC ..... Plt./373
CPC ..... A01H 6/10; A01H 5/00; A01H 5/02
See application file for complete search history.

*Primary Examiner* — Keith O. Robinson
(74) *Attorney, Agent, or Firm* — C. A. Whealy

(57) ABSTRACT

A new and distinct cultivar of *Caladium* plant named 'Bottle Rocket', characterized by its intermediate to tall height and upright plant habit; vigorous growth habit and rapid growth rate; fancy-type leaves that have dark green-colored margins, transitional areas that are white, dark green and red purple, red purple-colored venation and the areas adjacent to the veins and interveinal areas that are white, red purple and green; petioles that are tan pink in color with a dark brown caste; and tolerance to high light conditions.

4 Drawing Sheets

Botanical designation: *Caladium* X *hortulanum*.
Cultivar denomination: 'BOTTLE ROCKET'.

BACKGROUND OF THE INVENTION

The present invention relates to a new and distinct cultivar of *Caladium* plant, botanically known as *Caladium* X *hortulanum*, commercially referred to as a fancy leaf-type *Caladium* and hereinafter referred to by the name 'Bottle Rocket'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2010 in Avon Park, Fla. of *Caladium* X *hortulanum* 'White Christmas', not patented, as the female, or seed, parent with *Caladium* X *hortulanum* 'Creamsickle', disclosed in U.S. Plant Pat. No. 23,991, as the male, or pollen, parent. The new *Caladium* plant was discovered and selected by the Inventor as a single plant within the progeny of the stated cross-pollination in a controlled outdoor nursery environment in Zolfo Springs, Fla. in September, 2011.

Asexual reproduction of the new *Caladium* plant by "chipping" the tubers (cutting the tuber into segments with each segment containing an axillary bud and tuber cortical tissue) in a controlled outdoor nursery environment in Zolfo Springs, Fla. since April, 2012 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Bottle Rocket'. These characteristics in combination distinguish 'Bottle Rocket' as a new and distinct *Caladium* plant:

1. Intermediate to tall in height and upright plant habit.
2. Vigorous growth habit and rapid growth rate.
3. Fancy-type leaves that have dark green-colored margins, transitional areas that are white, dark green and red purple, red purple-colored venation and the areas adjacent to the veins and interveinal areas that are white, red purple and green.
4. Petioles that are tan pink in color with a dark brown caste.
5. Tolerant to high light conditions.

Plants of the new *Caladium* differ primarily from plants of the female parent, 'White Christmas', in the following characteristics:

1. Plants of the new *Caladium* and 'White Christmas' differ in leaf color as leaves of 'White Christmas' have distinct dark green-colored venation with white-colored interveinal areas that are often tinged with pink and dark green-colored borders.
2. Plants of the new *Caladium* and 'White Christmas' differ in leaf petiole color as plants of 'White Christmas' have green-colored leaf petioles with black-colored stripes.

Plants of the new *Caladium* differ primarily from plants of the male parent, 'Creamsickle', in the following characteristics:

1. Plants of the new *Caladium* and 'Creamsickle' differ in leaf color as leaves of 'Creamsickle' have greyed green-colored venation, greyed green and greyed purple-colored interveinal areas interspersed with dark green-colored sectors and borders.

2. Plants of the new *Caladium* and 'Creamsickle' differ in leaf petiole color as plants of 'Creamsickle' have grey green-colored leaf petioles.

Plants of the new *Caladium* can be compared to plants of *Caladium* X *hortulanum* 'Celebration', disclosed in U.S. Plant Pat. No. 23,993. In side-by-side comparisons, plants of the new *Caladium* differ primarily from plants of 'Celebration' in the following characteristics:

1. Plants of the new *Caladium* and 'Celebration' differ in leaf color as leaves of 'Celebration' have dark red-colored venation with white-colored interveinal areas surrounded by dark green-colored borders.
2. Plants of the new *Caladium* and 'Celebration' differ in leaf petiole color as leaf petioles of 'Celebration' are black in color with tan pink-colored stripes.

Plants of the new *Caladium* can be compared to plants of *Caladium* X *hortulanum* 'UF-172', disclosed in U.S. Plant Pat. No. 24,432. In side-by-side comparisons, plants of the new *Caladium* differ primarily from plants of 'UF-172' in leaf color as leaves of 'UF-172' have rose pink-colored venation and white and pink-colored interveinal areas surrounded by olive green-colored borders. In addition, leaf color pattern of leaves of the new *Caladium* are more distinct and contrasting than the leaf color pattern of leaves of plants of 'UF-172'.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet is a side perspective view of a typical plant of 'Bottle Rocket' in a container and grown in a shadehouse (tuber de-eyed).

The photograph at the top of the second sheet is a comparison view of typical potted plants of the female parent, 'White Christmas' (right), 'Bottle Rocket' (center) and the male parent, 'Creamsickle' (left).

The photograph at the bottom of the second sheet is a comparison view of typical potted plants of 'UF-172' (left), 'Bottle Rocket' (center) and 'Celebration' (right).

The photograph at the top of the third sheet is a comparison view of typical plants of 'Bottle Rocket' grown in containers; the plant on the left has not had its tuber de-eyed and the plant on the right has had its tuber de-eyed prior to planting.

The photograph at the bottom of the third sheet is a side perspective view of typical plants of 'Bottle Rocket' grown in an open field.

The photograph at the top of the fourth sheet is a close-up view of typical freshly-harvested tubers with roots and leaf petioles of 'Bottle Rocket'.

The photograph at the bottom of the fourth sheet is a close-up view of a typical inflorescence of 'Bottle Rocket'.

DETAILED BOTANICAL DESCRIPTION

The aforementioned photographs and following observations and measurements describe plants grown in 15-cm containers in a polypropylene-covered shadehouse (50% light reduction) in Avon Park, Fla. and plants grown in ground beds under full sunlight conditions in an outdoor nursery in Crewsville, Fla. The plants were grown under cultural practices typical of commercial shadehouse and outdoor nursery production. During the production of the shadehouse-grown plants, day temperatures ranged from about 28° C. to 33° C., night temperatures ranged from about 22° C. to 25° C. and light levels were about 8,000 foot-candles. During the production of the outdoor nursery-grown plants, day temperatures ranged from about 29° C. to 35° C., night temperatures ranged from about 23° C. to 26° C. and light levels were about 10,000 to 12,000 foot-candles. Plants grown in the shadehouse were eight weeks old and plants grown in the outdoor nursery were 7.5 months old when the photographs and the detailed description were taken. In the following description, color references are made to The Royal Horticultural Society Colour Chart, 2001 Edition, except where general terms of ordinary dictionary significance are used.

Botanical classification: *Caladium* X *hortulanum* 'Bottle Rocket'.

Parentage:

*Female, or seed, parent.*—*Caladium* X *hortulanum* 'White Christmas', not patented.

*Male, or pollen, parent.*—*Caladium* X *hortulanum* 'Creamsickle', disclosed in U.S. Plant Pat. No. 23,991.

Propagation:

*Type.*—By "chipping" the tubers.

*Time to initiate roots, summer.*—About seven to ten days at temperatures about 32° C.

*Time to initiate roots, winter.*—About two to three weeks at temperatures about 24° C.

*Tuber description* (*outdoor nursery-grown plants*).—Appearance: Multi-segmented; individual segments round to ovate in shape. Height: About 3.7 cm. Diameter: About 5.1 cm to 6.7 cm. Segment height: About 2.3 cm. Segment diameter: About 2.3 cm. Axillary buds size: About 4 mm by 6 mm. Texture: Thick, starchy; somewhat brittle. Color: Epidermis, freshly-harvested: Close to 199A, N199D and 158D. Epidermis, dried: Close to 200A. Cortical tissue: Close to 155A and 8D. Axillary buds: Close to 37D. Root description: Thick, fleshy contractile roots with few lateral branches; color, close to 155C. Rooting habit: Medium density.

Plant description:

*Plant type.*—Herbaceous perennial; suitable as a potted plant in containers 15-cm to 25-cm and suitable as a landscape plant in shaded and sunlit areas.

*Plant and growth habit.*—Intermediate to tall in height and upright plant habit; vigorous growth habit and rapid growth rate; potted plants in finished or saleable form in about seven to eight weeks after planting tubers; leaf petioles and leaves arise from one or more growing points on tubers; leaf petioles initially upright and outwardly leaning with development.

*Plant height, from soil level to top of foliar plane, shadehouse-grown potted plants.*—About 33 cm to 40 cm.

*Plant height, from soil level to top of inflorescences, shadehouse-grown potted plants.*—About 31.5 cm.

*Plant diameter or spread, shadehouse-grown potted plants.*—About 32 cm to 42 cm.

*Number of shoots per plant, shadehouse-grown potted plants, tubers not de-eyed.*—About two develop per #1 tuber.

*Number of shoots per plant, shadehouse-grown potted plants, tubers de-eyed.*—About three to four develop per #1 tuber.

*Cataphylls, shadehouse-grown potted plants.*—Length: About 6.2 cm to 10 cm. Width: About 1.6 cm to 2.4 cm. Shape: Wedge-shaped. Apex: Acuminate to emarginate. Base: Sheathing the stem. Color, inner surface: Close to N155C faintly tinged with close to 182D; colors and patterns on the outer surface are visible on the inner surface. Color, outer surface: Close to N170D and 82D variably streaked and stippled with close to 200B; with development, color becoming closer to 199B faintly tinged with close to 187B.

Leaf description:

*Arrangement and type.*—Alternate; simple; fancy-type.

*Length, shadehouse-grown potted plants.*—About 20 cm to 31 cm.

*Width, shadehouse-grown potted plants.*—About 11.5 cm to 20 cm; when flattened, about 12.2 cm to 21 cm.

*Shape.*—Ovate.

*Apex.*—Acute to acuminate.

*Base.*—Sagittate to peltate.

*Margin.*—Entire; wavy with broad undulations.

*Texture and luster, upper and lower surfaces.*—Smooth, glabrous; dull sheen.

*Texture and luster, lower surface.*—Smooth, glabrous; slightly glaucous and dull sheen.

*Venation pattern.*—Pinnate.

*Color, shadehouse-grown potted plants.*—Developing and fully developed leaves, upper surface: Background color: Close to 147A with random flecks and speckles, close to 155C and 145D, and random spots, close to 51B, 51C and 155C. Margins: Close to 147A; thin leaf edge, close to 187A. Basal notch: Close to 187A. Midvein and primary venation: Close to 185A surrounded with close to 53B, 53A and 147B tinged with close to 146B often with flecks, close to 155C and 145D. Secondary venation: Close to 183A tinged with close to 53A. Interveinal areas: Close to 155C, 155C variably flushed with close to 51C or 51D, or close to 147B tinged with close to 146B with speckles, close to 155C. Transitional areas: Close to 183A tinged with close to 53A. Developing and fully developed leaves, lower surface: Background color: Close to 191A. Margins: Close to 191A; thin leaf edge, close to 187A. Basal notch: Close to 187B. Midvein: Close to 195B to 195C tinged with close to 182D and streaked and flushed with close to 183D surrounded with close to 184B and 191A to 191C mottling. Primary venation: Close to 195B surrounded with close to 184B and 191A to 191C mottling. Interveinal and transitional areas: Random and variable sectors, close to 155C; close to 155C tinged with close to 146D; close to 155C flushed with close to 49B and 49C; close to 49B and 49C; close to 196B; and close to 196C tinged with close to 49C.

*Petioles.*—Aspect: Initially upright and straight and outwardly leaning with development; flexible. Length, shadehouse-grown potted plants: About 21 cm to 35 cm. Diameter, distally, shadehouse-grown potted plants: About 5 mm to 7 mm. Diameter, proximally, shadehouse-grown potted plants: About 7 mm to 10 mm. Texture: Smooth, glabrous. Color, shadehouse-grown potted plants: When developing and fully developed: Close to 182C, 182D and 181D streaked, stippled and slightly tessellated with close to 200B; proximally, close to 181D and 182D streaked, stippled and tessellated with close to 200B tinged with close to 147A; below the leaf and petiole junction, close to 147C flushed and streaked with close to 182B and 182C. Wing length, shadehouse-grown potted plants: About 5 cm to 9 cm. Wing diameter, shadehouse-grown potted plants: About 9 mm to 14 mm. Texture and luster, inner and outer surfaces: Smooth, glabrous; dull sheen. Wing color, shadehouse-grown potted plants: Inner surface: Close to N155B to N155C faintly tinged with close to 182D; colors and patterns on the outer surface are visible on the inner surface. Outer surface: Close to N170D, 159C and 182D stippled, streaked and tessellated with close to 200B tinged with close to 147A to 147B.

Inflorescence description: Inflorescences observed on eight week-old shadehouse-grown potted plants.

*Inflorescence arrangement.*—Upright hooded spathes surrounding a columnar spadix borne on a tall upright scape; spadix with sessile, simple female and male flowers separated into two zones; female flowers develop on the proximal one-third of the spadix; male flowers develop on the distal two-thirds of the spadix; sterile flowers develop at junction of female and male flower zones; near this junction, the spathe constricts and surrounds and encloses the female flowers; spathe open and cupped around male flowers.

*Fragrance.*—Night-fragrant; jasmine-like with camphor note.

*Natural flowering season and flower longevity.*—Plants of the new *Caladium* typically flower during the spring in central Florida; flowers develop about eight weeks after growth commences; inflorescences last about three days before fading; inflorescences persistent.

*Spathe.*—Length, overall: About 11.2 cm. Length, distal open portion: About 6.8 cm. Length, proximal closed portion: About 4.4 cm. Width, distal open portion: About 3 cm. Depth, distal open portion: About 2.8 cm. Width, at constriction: About 1.3 cm. Width, proximal closed portion: About 2.8 cm. Shape, open portion: Elliptic. Apex: Acute. Base: Obtuse. Margin: Entire; smooth. Texture, front and rear surfaces: Smooth, glabrous. Luster, front surface: Dull sheen. Luster, rear surface: Dull sheen; proximally, glaucous. Color, front surface: Distal open portion: Close to 155C and 145D; with development, color becoming closer to 199C and 199D. Proximal closed portion: Close to 147D and 148D; towards the base, faintly flushed with close to 187A; color does not change with development. Color, rear surface: Distal open portion: Close to 145C and 145D mottled with close to 155C; color does not change with development. Proximal closed portion: Close to 147B, 147C and 147D mottled with close to 148C and 148D variably tinged with close to 182D; color does not change with development.

*Spadix*.—Length, overall: About 8.2 cm. Length, male flower zone: About 4.2 cm. Length, sterile zone: About 1.8 cm. Length, female flower zone: About 2.2 cm. Diameter, male flower zone: About 1 cm. Diameter, sterile flower zone: About 7 mm. Diameter, female flower zone: About 9 mm. Shape: Columnar, spindle-shaped. Apex: Rounded. Base: Obtuse. Aspect: Upright. Color, mature, male zone: Close to 11D. Color, mature, sterile zone: Close to 158D. Color, mature, female zone: Close to 158C. Male flowers: Quantity per spadix: About 126. Shape: Obovate. Height: About 2.5 mm. Diameter: About 3 mm. Pollen amount: Sparse. Pollen color: Close to 10D. Female flowers: Quantity per spadix: About 220. Shape: Obovate. Height: About 2 mm. Diameter: About 1.5 mm. Stigma color: Close to 159C. Ovary color: Close to 159C tinged with close to N170D.

*Scape*.—Length: About 21.3 cm. Diameter: About 6 mm. Strength: Sturdy; flexible. Aspect: Mostly erect. Texture and luster: Smooth, glabrous; dull sheen; distally, glaucous. Color: Close to 147A and 147B variably tinged with close to 182D and stippled and streaked with close to 200C to 200D; distally, close to 147C and 147D tinged with close to 182D and faintly and variable streaked and tinged with close to 200C.

*Seeds and fruits*.—To date, seed and fruit development have not been observed on plants of the new *Caladium*.

Pathogen & pest tolerance: Plants of the new *Caladium* have been observed to have average tolerance to *Pythium* Root Rot and above average tolerance to *Xanthomonas* Leaf Spot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and are suitable for USDA Hardiness Zones 8A to 11. In cooler zones, tubers can be "lifted" prior to first freeze and stored in a cool dry environment to overwinter for re-planting the following spring.

It is claimed:

1. A new and distinct *Caladium* plant named 'Bottle Rocket' as illustrated and described.

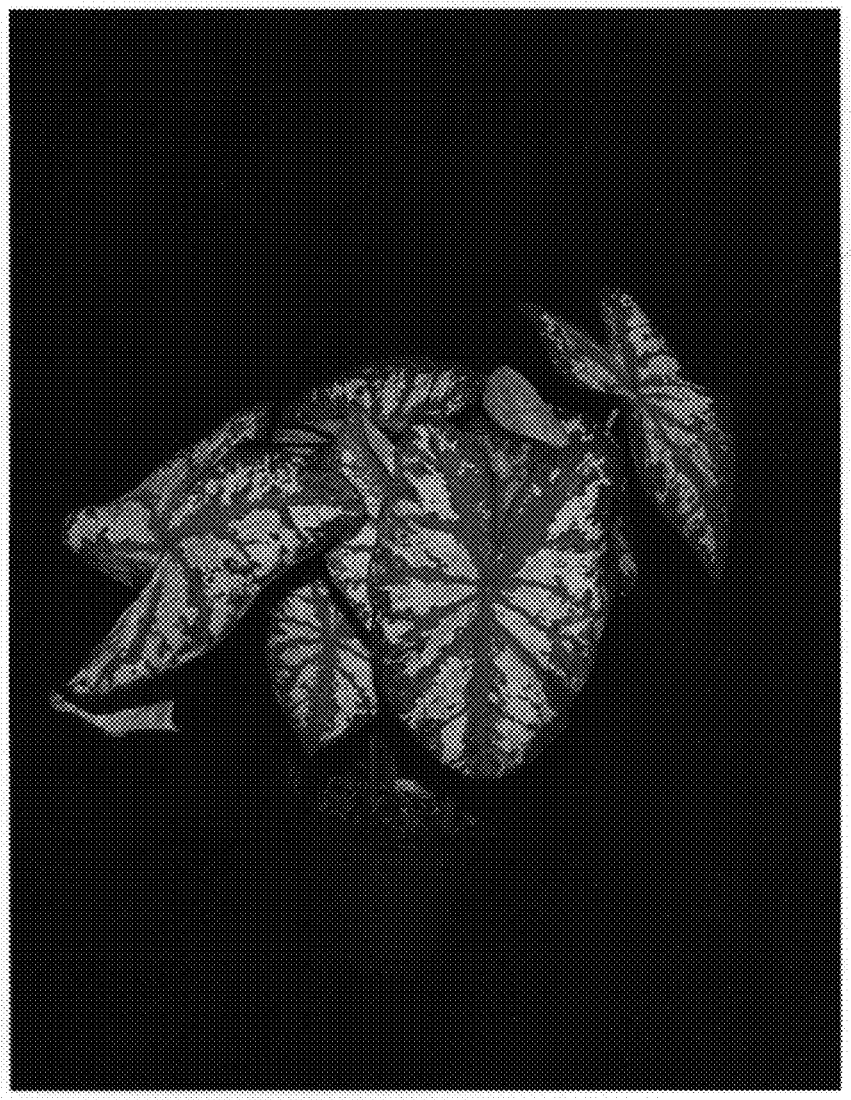

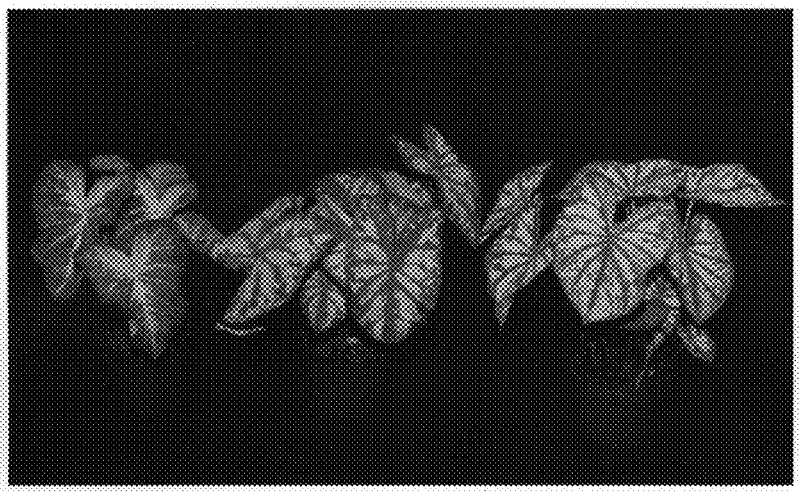
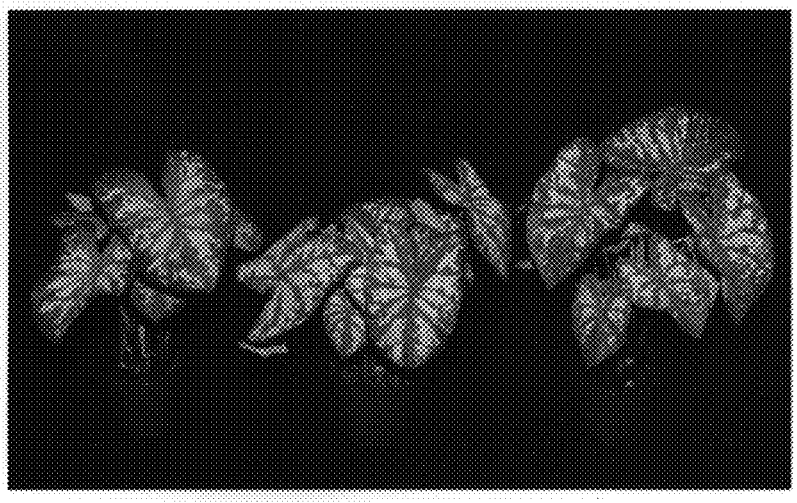

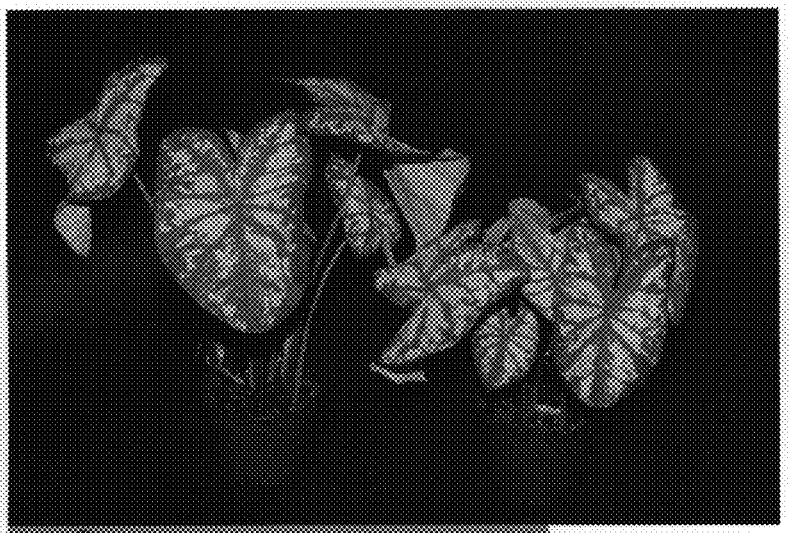
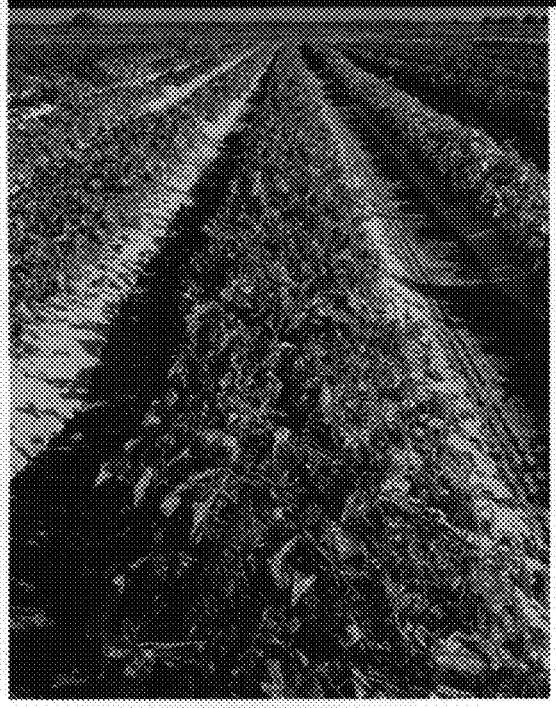

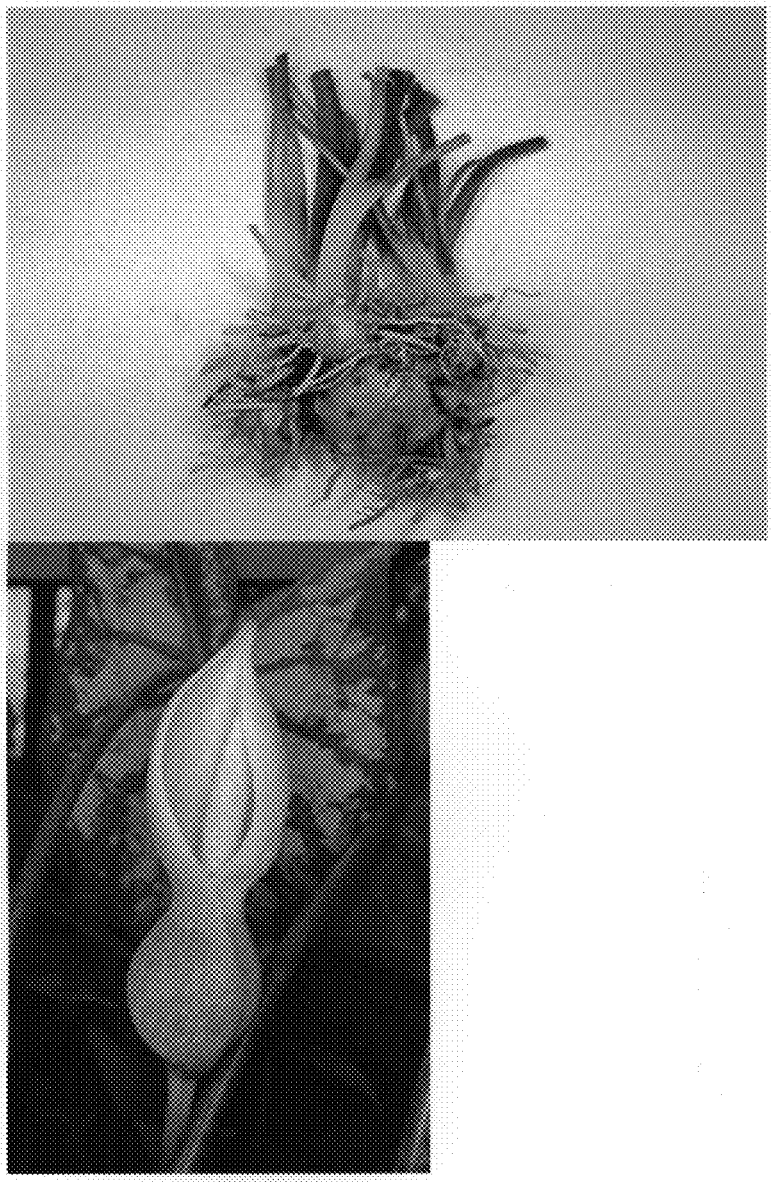

* * * * *